United States Patent [19]

Schlüter et al.

[11] Patent Number: 4,765,895

[45] Date of Patent: Aug. 23, 1988

[54] APPARATUS FOR RECOVERY OF CELL MATERIAL FROM BODY FLUIDS

[75] Inventors: Gert Schlüter, Gundelfingen; Erwin Albrecht, Freiburg, both of Fed. Rep. of Germany

[73] Assignee: Sarstedt, Numbrecht-Rommelsdorf, Fed. Rep. of Germany

[21] Appl. No.: 562,852

[22] Filed: Dec. 19, 1983

[30] Foreign Application Priority Data

Dec. 27, 1982 [DE] Fed. Rep. of Germany ....... 3248214

[51] Int. Cl.⁴ .............................................. B01D 39/08
[52] U.S. Cl. .................................... 210/491; 210/507; 210/927
[58] Field of Search ................ 210/507, 484, 488–491, 210/927

[56] References Cited

U.S. PATENT DOCUMENTS 4,056,476 11/1977 Mouwen et al. .................... 210/507

Primary Examiner—Tom Wyse
Attorney, Agent, or Firm—Bucknam and Archer

[57] ABSTRACT

An apparatus for the recovery of cell material from body fluids is described which consists of a filter with a filter material arranged in one or more layers and not soluble in cell-fixing liquids, such as isopropanol. The filter material consists of a single textured or crimped filament yarn. Preferably, the filaments of the filament yarn are made of synthetic polymers. In contrast to the known apparatus, consisting essentially of a filter cartridge which contains as filter material synthetic fibers dissolvable in alcohol or in an alcohol-water mixture, the use of the apparatus of this invention produces a cell sample which is not interspersed with particles of the filter material. Besides, the present invention permits to achieve very low cell losses, and cell damage does not occur. Body fluids from which cell material may be recovered with the apparatus according to this invention are for example, urine, liquor, pleural effusions or fluids from the abdomen area.

3 Claims, No Drawings

APPARATUS FOR RECOVERY OF CELL MATERIAL FROM BODY FLUIDS

The invention relates to an apparatus for recovery of cell material from body fluids. The apparatus consists of a filter with a filter material arranged in one or more layers and not soluble in cell-fixing liquids.

For the detection of diseases and in particular malignant degenerations in the human body in an early stage, the diagnostics of cellular components from specific organs occupies an eminent position. For this purpose, cells are recovered from surfaces of the organs by smear procedures;

from deeper regions of the organs by biopsy and puncture procedures;

from body fluids, namely physiologically present body fluids, such as urine or other fluids, or body fluids formed by pathological processes, such as pleural discharges, fluid from the abdomen, by centrifugation or by filtration with the aid of membrane filters.

The known methods and devices for the recovery of cells from body fluids have the disadvantage that either a fixation of the cells is effected in the sampled or precipitated body fluids, not immediately, but only after additional operations so that additional cell damage is caused in the operation or recovery process.

A serious drawback is the high loss rate during centrifugation, because up to 40% of the cell material present in the body fluid may be lost by adhesion to the walls of centrifugation vessels, etc. Filtration, with the aid of filter membranes, requires, as a rule, suction or pressure procedures, which may create additional artifacts at sensitive or predamaged cells. Another disadvantage is that e.g. in urine samples, practically never the total fluid miction may be worked up because of the high cost. This means that only a part of the liquid, as a rule up to 20 ml, is filtered, with the result for samples of low cell count that the slide is insufficiently covered.

German Offenlegungsschrift No. 31 08 133 describes a method and an apparatus according to which these disadvantages may be avoided.

The known method for testing urine for particulates, in particular for cells, consists of passing the urine, immediately after precipitation or sampling, through a filter of synthetic fibers which are dissolvable in alcohol or in an alcohol-water mixture, and after the fibers are dissolved in a cell-fixing solvent, the sample, i.e. the cells collected by filtration, is kept in this solvent until the analysis is made. The known apparatus consists essentially of a filter cartridge which contains as filter material synthetic fibers dissolvable in alcohol or in an alcohol-water mixture.

Although such a fiber-stuffed filter cartridge has a good filtering action, the disadvantage is that when for example, ethyl cellulose fibers are used as filter material for the filter cartridge, these fibers are not completely dissolved, so that the cell sample is interspersed with a considerable proportion of undissolved ethyl cellulose particles which appear in the slide preparation, after the step of staining the cells required for the microscopic analysis, as an homogeneous diffused background.

Reduction of the undissolved ethyl cellulose particles in the cell sample is possible only by repeated washing operations in a large quantity of high-percentage alcohol, so that centrifugation steps are, in addition, necessary.

Further, it is know to recover cell material from body fluids by filtration with the aid of filter mats. While such filter mats also have a good filtering action, the recovery of the cell material from the mat is very difficult, so that high cell losses occur.

Filter fabrics for the recovery of cell material from body fluids, on the other hand, have the disadvantage that their filtration efficiency is poor, so that too much cell material runs through the filter fabric.

An object of the invention is to provide an apparatus for the recovery of cell material from body fluids which avoids the disadvantages of the known apparatuses described hereinabove.

The problem is solved in an apparatus for the recovery of cell material from body fluids of the type described hereinabove which comprises a filter with a material arranged in one or more layers, the filter material not being soluble in cell-fixing liquids. The filter material consists of a single textured or crimped filament yarn.

An advantageous embodiment of the apparatus according to the invention resides in the use of synthetic polymers for the filaments of the filament yarn.

Within the scope of this invention, are suitable as filaments for the filament yarns, for example polyolefin, such as polypropylene yarns;

polyester, such as polyethylene terephthalate; and/or polyamide, such as polyamide -6,6 yarns.

Filament yarns suitable for the apparatus according to the invention, are those which have been produced by texturing or crimping, for example by false twist texturing, tuyere crimping or compression chamber crimping.

The invention will be illustrated more specifically with reference to an example.

EXAMPLE

For the preparation of the apparatus according to the invention, a cylindrical tube of polypropylene was used. The tube had a length of 40 mm and an inner diameter of 7 mm.

On one side, the tube was provided with a fixed cylindrical inner ring of a length of 5 mm and an inner diameter of 4.5 mm.

On the other side, the tube was provided with a plug of a metal mesh of a mesh width of 0.35 mm. The plug extended 10 mm into the tube and had a firm seat in the tube. The tube was then inserted from the plug side to a depth of 5 mm into a vacuum hose connected with a vacuum pump so as to be firmly seated flush with the wall. On the side of the tube provided with the cylindrical inner ring, a suction nozzle was applied, consisting of a cylindrical metal tube of a length of 100 mm and an inner diameter of 1.5 mm. The tube and the suction nozzles were joined together sealingly by a plastic sleeve partially overlapping both the tube and the suction nozzle.

By means of the vacuum pump, the tube was then evacuated to a vacuum of 0.82 bar ($=8200$ N/m$^2$). Afterwards, the end of a filament yarn drawn from a spool and passed over an adjustable proportioning device was applied at the free opening of the suction nozzle. In view of the vacuum, the filament yarn was sucked into the tube in the amount of 50 mgs through the suction nozzle and deposited on the plug of metal mesh in several layers. Afterwards, the tube was separated from the vacuum hose and from the nozzle and the plug removed from the metal mesh away from the tube.

Instead of the plug of metal mesh, a cylindrical sleeve of polypropylene of 27 mm length, inner diameter of 6 mm and an outside diameter such that the sleeve could be inserted into the tube and firmly seated in the tube was inserted into the tube over a length of 27 mm. The cylindrical sleeve had an externally corrugated hollow-cylindrical top of outer diameter of 10 mm, so that one edge of this top rested on the edge of the tube. The inner diameter of the top matched rhat of the sleeve.

The filament yarn accumulated in the tube was compressed to a length of 8 mm by the inner ring and the cylindrical sleeve. Over this length of 8 mm, the filament yarn was homogeneously distributed in the tube.

As filament yarn, a false twist textured polyethylene terephthalate filament yarn 50 dtex f 22×1 S was used, the filaments of which had a trilobal cross-section. The filament yarn had the following crimp values according to DIN 53840:

crimp elasticity: 36%
crimp stability : 77%.

The tube was connected with a laboratory glass funnel through a hose.

Thereafter, a cell-containing urine sample of a total miction was run across the funnel through the tube. After the entire urine sample had run through the tube, the tube was disconnected from the hose piece and the cylindrical sleeve was removed from the tube. Thereafter, the tube was closed with a cap on the side provided with the cylindrical inner ring. By its open side, the tube was sealingly connected with a cylindrical tubular vessel of inner diameter 12 mm and length 80 mm. The vessel was closed with a plug on the opposite side and contained 5 ml of 30% isopropanol. The vessel and tube connected with it were then shaken for 10 seconds. In this process, the filament yarn was soaked with isopropanol. Under the influence of the isopropanol on the filament yarn as well as due to the shaking process, the crimps of the filaments of the yarn opened, and as a result, the yarn swelled and loosened from its compressed condition. The filament yarn, therefore, distributed itself over the total volume of the vessel. The result was that the cell material adhering to the yarn through the filtering process transferred into the isopropanol and was, at the same time, fixed. To separate the filament yarn from the cell suspension, first the tube was disconnected from the vessel, the vessel being held vertically with the plug down. Thereafter, the filament yarn was gripped with dissecting forceps or with a rod roughened at its end and was squeezed by rotational motions and simultaneous pressing against the vessel wall above the surface of the liquid, whereby the remaining isopropanol and still adhering cells were separated from the filament yarn to a large extent. Then, the vessel was left standing vertically with the plug down, whereby the cell material present in the isopropanol was caused to settle. After completing the sedimentation, the supernatant isopropanol was decanted. The cell sediment was taken up either with a pipette or with a record injection syringe and transferred to a slide. It was found that in this way, 95% of the cells present in the urine sample having a diameter of 7 $\mu$m and higher, could be recovered therefrom undamaged. With a corresponding mat filter of crimped cellulose-2,5-acetate fibers used for comparison, only 60% of the cells having a diameter of 7 $\mu$m and higher could be recovered from a similar urine sample.

The present invention offers the following advantages:

The apparatus according to the present invention permits to avoid costly centrifugation steps.

With the apparatus of the present invention, no cell damage occurs; besides, larger losses of cells are avoided.

When using the apparatus according to the invention, the cell sample obtained is not interspersed with fragments or residues of the filter material.

The apparatus according to the invention permits the fixation of the obtained cells immediately after the filtration.

With the apparatus according to the invention, a filtering action equally good as with a mat filter is obtained, but much more cell material is recovered, and this is the result of the swelling of the filament yarn in the cell-fixing liquid.

What is claimed is:

1. Apparatus for recovery of cell material from body fluids, consisting of a filter with a filter material arranged in one or more layers and not soluble in cell-fixing liquids, wherein the filter material consists of a single compressed textured or crimped filament yarn and wherein the filaments of the filament yarn consist of a synthetic polymer.

2. The apparatus according to claim 1 wherein the synthetic polymer is a polyolefin, a polyester or a polyamide.

3. The apparatus according to claim 1 wherein the filament yarn is a false twist textured polyethylene terephthalate filament yarn.

* * * * *